United States Patent
Wang

(10) Patent No.: US 6,849,278 B2
(45) Date of Patent: Feb. 1, 2005

(54) **METHOD TO COUNTER OXIDATION OF LDL, DECREASE TRIGLYCERIDE OR CHOLESTEROL AND INHIBIT ATHEROSCLEROSIS USING *HIBISCUS SABDARIFFA* EXTRACT**

(75) Inventor: Chau-Jong Wang, Taichung (TW)

(73) Assignee: Universal Biotech Co., Ltd., Kaohsiung (TW)

( * ) Notice: Subject to any disclaimer, the term of this patent is extended or adjusted under 35 U.S.C. 154(b) by 0 days.

(21) Appl. No.: 09/989,490

(22) Filed: Nov. 21, 2001

(65) Prior Publication Data

US 2003/0096021 A1 May 22, 2003

(51) Int. Cl.⁷ .............................................. A61K 35/78
(52) U.S. Cl. ...................................................... 424/725
(58) Field of Search ......................................... 424/725

(56) References Cited

U.S. PATENT DOCUMENTS 6,113,949 A * 9/2000 Brink
6,127,553 A * 10/2000 Ibnusaud et al.
6,271,001 B1 * 8/2001 Clarke et al.

FOREIGN PATENT DOCUMENTS

| CN | 1156552 | * | 8/1997 |
| FR | 2454277 | * | 12/1980 |
| JP | 56029522 | * | 3/1981 |
| JP | 09295928 | * | 11/1997 |
| JP | 2000095663 | * | 4/2000 |
| JP | 2000154134 | * | 6/2000 |
| JP | 2000239164 | * | 9/2000 |

OTHER PUBLICATIONS

Tamaki et al., Mokuzai Gakkaishi, 2001, 47(2), 159–63.*

* cited by examiner

*Primary Examiner*—Michael Meller
(74) *Attorney, Agent, or Firm*—Birch, Stewart, Kolasch & Birch, LLP

(57) ABSTRACT

A method for countering oxidization of low density lipoproteins, reducing cholesterol or triglyceride in plasma or inhibiting atherosclerosis comprising administering an effective amount of a *Hibiscus sabdariffa* extract.

4 Claims, 12 Drawing Sheets

(1 of 12 Drawing Sheet(s) Filed in Color)

| Treatment | | |
|---|---|---|
| ox-LDL inducer | Conc. of HSE (mg/ml) | TBARs formation (nmol/mg) |
| Control | - | 0.19 ±0.01 |
| $CuSO_4$ | - | 10.12 ±0.49 |
| $CuSO_4$ | 0.5 | 8.47 ±1.00 |
| $CuSO_4$ | 1 | 5.61 ±0.56* |
| $CuSO_4$ | 2 | 0.56 ±0.04** |

FIG. 3

| Treatment | | TBARs formation (nmol / mg) |
| --- | --- | --- |
| ox - LDL inducer | Conc. of HSE (mg/ml) | |
| Control | - | 0.19 ±0.01 |
| CuSO$_4$ | - | 10.41 ±1.02 |
| CuSO$_4$ | 0.5 | 8.90 ±0.20 |
| CuSO$_4$ | 1 | 5.53 ±1.31* |
| CuSO$_4$ | 2 | 0.60 ±0.05** |

FIG. 4

| Hepatic function | Rabbit | | Rat | |
| --- | --- | --- | --- | --- |
| | Basal diet | HSE 1 % | Basal diet | HSE 2 % |
| ALT(UL/l)[a] | 55.25±23.87 | 40.83±11.99 | 55.8±19.18 | 34.2±9.44 |
| AST(UL/l) | 98.75±34.09 | 89.50±55.49 | 108.8±20.85 | 67.7±11.06 |
| ALP(UL/L) | 38.00±3.83 | 26.83±9.56 | 121.0±101.0 | 103.0± 85.0 |

FIG 11

| Hepatic function | Rabbit | | Rat | |
| --- | --- | --- | --- | --- |
| | Basal diet | HSE 1 % | Basal diet | HSE 2 % |
| BUN (mg/dl)[a] | 16.12 ± 4.7 | 30.10 ± 17.2 | 14.6±5.13 | 19.0±6.42 |
| Creatinine (mg/dl) | 1.65±0.29 | 1.50 ± 0.40 | 0.54±0.13 | 0.73±0.10 |
| UA (mg/dl) | 0.18±0.15 | 0.23±0.16 | 1.9±0.68 | 1.65±0.37 |

FIG 12

METHOD TO COUNTER OXIDATION OF LDL, DECREASE TRIGLYCERIDE OR CHOLESTEROL AND INHIBIT ATHEROSCLEROSIS USING *HIBISCUS SABDARIFFA* EXTRACT

BACKGROUND OF THE INVENTION

1. Field of the Invention

The present invention relates to the novel applications of the *Hibiscus sabdariffa* extract in countering oxidization of low density lipoproteins, reducing cholesterol or triglyceride in plasma or inhibiting atherosclerosis.

2. Description of the Related Art

Conventionally, *Hibiscus sabdariffa* is a local soft drink material and medical herb demonstrating analgesic and antipyretic effects and can be used to cure liver-complaint. The past studies showed that *Hibiscus sabdariffa* possesses analgesic activity as well as antipyretic and anti-inflammatory action American Journal of Chinese Medicine, Vol. XXIV, Nos. 3–4, pp. 263–269, antispasmodic potential Journal of Ethnopharmacology, 31 (1991) 249–257 Elsevier Scientific Publishers Ireland Ltd., antimutagenic and chemo-preventive activity Food and Chemical Toxicology 37 (1999) 591–601, antioxidant activity Food and Chemical Toxicology 35 (1997) 1159–1164 and is able to quench the free radicals of 1,1-diphenyl-2-picrylhydrazyl Food and Chemical Toxicology 38 (2000) 411–416 and lower high blood pressure Journal of Ethnopharmacology v.65(3) JUNE 1999 P. 231–236.

SUMMARY OF THE INVENTION

The vessel-related diseases such as apoplexy and heart attack have been the major causes of death in many countries. Though vessel-related diseases are caused by interactions of many factors, atherosclerosis has been the major factor contributing to vessel-related diseases according to the previously published literature.

Viewing of the above, the inventor scanned plants and herbs and finally discovered *Hibiscus sabdariffa* extract could be applied in decreasing cholesterol or triglyceride levels in plasma, countering oxidation of low density lipoproteins, and inhibiting the abnormal growth of smooth muscle cells or endothelium cells.

Accordingly, it is an object of the present invention to provide with a method of countering oxidization of low density lipoproteins comprising administering an effective amount of a *Hibiscus sabdariffa* extract.

Another object of the present invention is to provide with a method of decreasing cholesterol or triglyceride levels in plasma comprising administering an effective amount of a *Hibiscus sabdariffa* extract.

Another object of the present invention is to provide with a method of inhibiting atherosclerosis comprising administering an effective amount of a *Hibiscus sabdariffa* extract.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objects, features, and advantages of the present invention will become apparent upon consideration of the detailed description of the presently-preferred embodiments, when taken in conjunction with the accompanying drawings wherein:

FIG. 3 is a table showing Pretreatment effect of HS on the $CuSO_4$ induced lipid peroxidation in LDL. * $p>0.001$; ** $p>0.00001$, compared with CuSO.sub.4 treated LDL group;

FIG. 4 is a table showing Post-treatment effect of HSE on the $CuSO_4$ induced lipid peroxidation in LDL. * $p<0.01$; ** $p<0.0001$, compared with CuSO.sub.4 treated alone group;

FIG. 11 is a table showing Effect of HSE on hepatic function in rabbit and rat[a] Abbreviation, ALT, alanine transaminase; AST, aspartate aminotransferase; ALP, alkaline phosphatase;

[a]Abbreviation, BUN, blood urea nitrogen; UA, uric acid.

FIG. 12 is a table showing Effect of HSE on renal function in rabbit and rat.

DETAIL DESCRIPTION OF THE PREFERRED EMBODIMENT

The preferred embodiment of the present invention provides a method which uses *Hibiscus sabdariffa* extract to counter oxidization of low density lipoproteins. The preferred embodiment of the present invention also provides a method to decrease triglyceride or cholesterol levels in plasma. The preferred embodiment of the present invention further provides a method to inhibit atherosclerosis. According to the present invention it has beneficially found that *Hibiscus sabdariffa* extract contains natural compounds which have a preventive effect on vessel-related diseases.

The *Hibiscus sabdariffa* extract is constituted by removing the active constituents from the calyxes or petals of *Hibiscus sabdariffa* through a water extraction process. The *Hibiscus sabdariffa* extract may be concentrated or dried if necessary. The dosage range for a *Hibiscus sabdariffa* extract to be used by humans have an overall general range of 5 to 50 g per day, a preferred range of 10 to 30 g per day and a specific daily dosage of 20 g per day.

The following examples further illustrate the present invention. They are not intended to limit the scope of the invention. Various modifications, alternative constructions and equivalents may be employed without departing from the true spirit and scope of the invention.

EXAMPLE 1

Countering Oxidation of LDL

Figure 1:
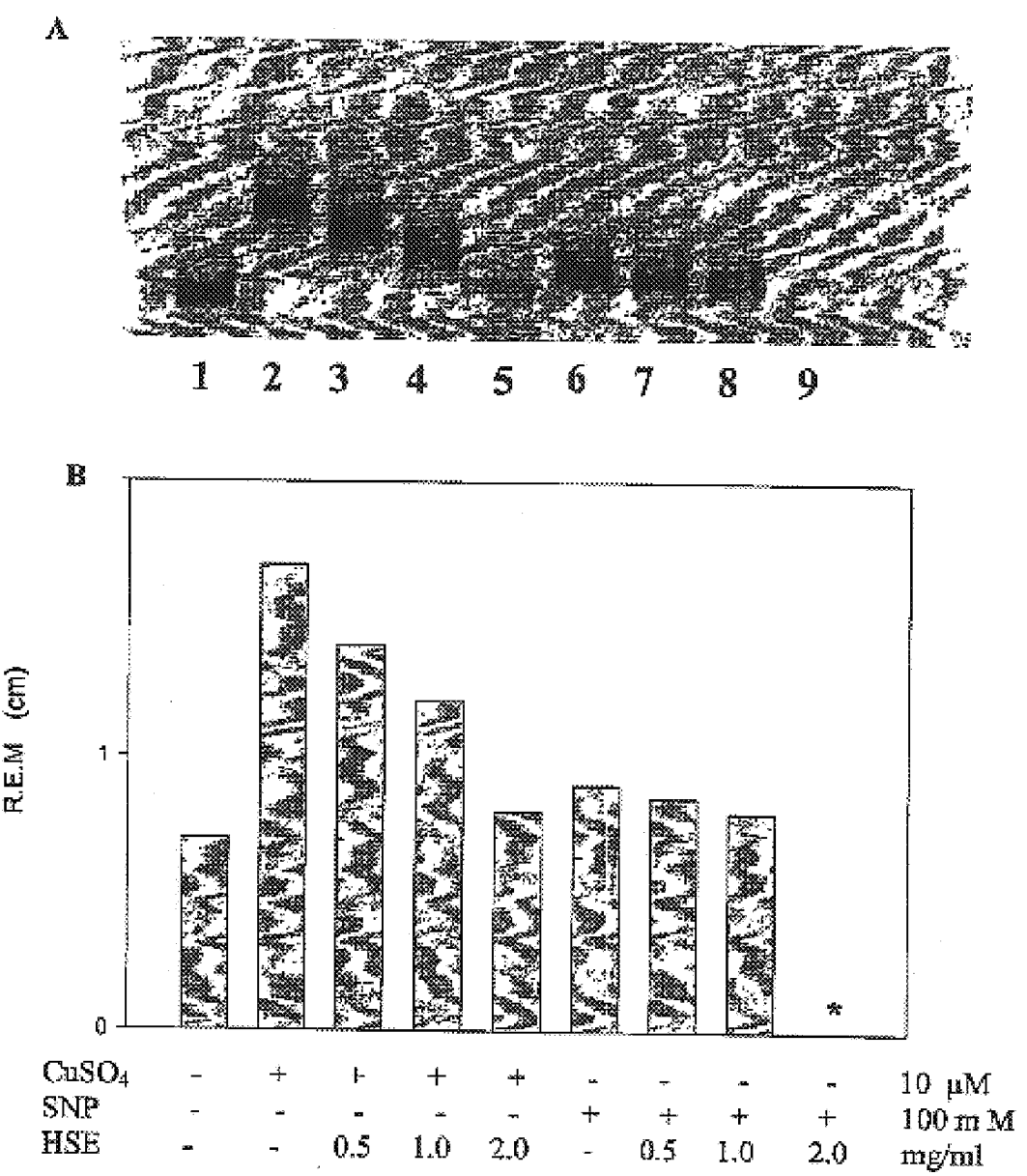
FIG. 1 is a graph wherein (A) shows Agarose gel electrophoresis of low density lipoprotein (hereinafter referred to as "LDL"). LDL was incubated with $CuSO_4$ or Sodium Nitroprusside (hereinafter referred to as "SNP") for 24 hours at 37° C. The sample on the gel lanes are follows: lane 1, native LDL; lane 2, LDL incubated with $CuSO_4$; lane 3–5, LDL incubated with $CuSO_4$ in the presence of 0.5 (lane 3), 1 (lane4) and 2 mg/ml (lane5) Hibiscus sabdariff a extract (hereinafter referred to as "HSE"); lane 6, LDL incubated with SNP; lane 7–9, LDL incubated with SNP in the presence of 0.5 (lane7), 1 (lane8) and 2 mg/ml(lane9) HSE; (8) shows Determination of relative electrophoretic mobility. * LDL degradation.

The molecular weight of LDL is smaller when LDL has not been oxidated, therefore, the mobility is greater in the SDS-PAGE experiment under the same potential. Comparatively, the molecular weight of LDL is larger when LDL has been oxidized, therefore, the mobility is lower in the SDS-PAGE experiment under the same potential. After LDL being incubated with 10 $\mu$M $CuSO_4$ or 100 mM SNP for 24 hours at 37° C. respctively in the presence of various concentrations of HSE, it is observed that the higher the concentration of HSE is, the more significantly the oxidation of LDL is countered. The results are shown in FIG. 1.

Figure 2:
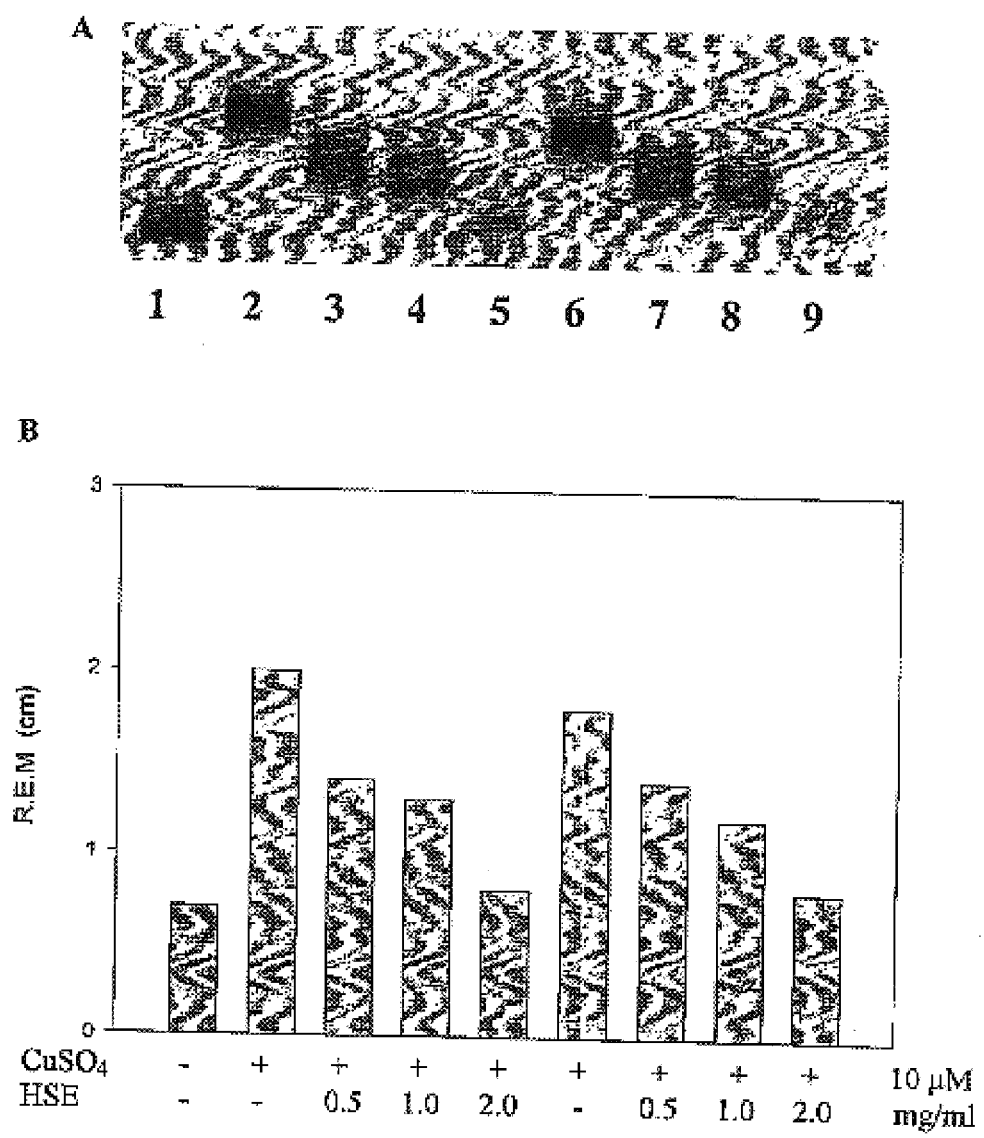
FIG. 2 is a graph wherein (A) shows Agarose gel electrophoresis of LDL. LDL was incubated with $CuSO_4$ for 24 hours at 37° C. The sample on the gel lanes are follows: lane 1, native LDL; lane 2, LDL incubated with $CuSO_4$; lane 3–5, LUL incubated with $CuSO_4$ in the presence of 0.5 (lane3), 1 (lane4), 2 mg/ml(lanes) HSE; lane 6, LDL pre-incubated with $CuSO_4$; lane 7–9, LDL pre-incubated with $CuSO_4$ than addition of 0.5 (lane7), 1 (lane8) and 2 mg/rnl(lane9) HSE; (8) shows Determination of relative electrophoretic mobility.

We can learn from the above that the oxidation of LDL incubated with $CuSO_4$ or SNP will be countered in the presence of HSE. It is also observed that adding HSE after LDL was pre-incubated with $CuSO_4$ for 24 hours at 37° C. is helpful in countering the oxidation of LDL. In addition, the higher the concentration of HSE is, the more significantly the oxidation of LDL is countered. The results are shown in FIG. 2.

Additionally, LDL were pretreated with various concentrations of HSE for 5 minutes, and then incubated with 10 $\mu$M $CuSO_4$ for 24 hours at 37° C. Comparing with the control group, the measurements of the TBARs indicate that pretreatment with HSE can significantly reduce the formation of TBARs, the group pretreated with 1 mg/dl HSE outperformed the control group by 180% (P<0.01), the group pretreated with 2 mg/dl HSE outperformed the control group by 1800% (P<0.0000). The results are shown in FIG. 3.

Further, LDL were incubated with $CuSO_4$ 10 $\mu$M HSE for 5 minutes, and then post-treated with various concentrations of HSE for 24 hours at 37° C. The measurements of the TBARs indicate that post-treatment with HSE is able to decrease the formation of TBARs, the group post-treated with 1 mg/dl HSE outperformed the control group by 190% (P<0.01), the group post-treated with 2 mg/dl HSE outperformed the control group by 1700% (P<0.0001). The results are shown in FIG. 4.

Figure 5:
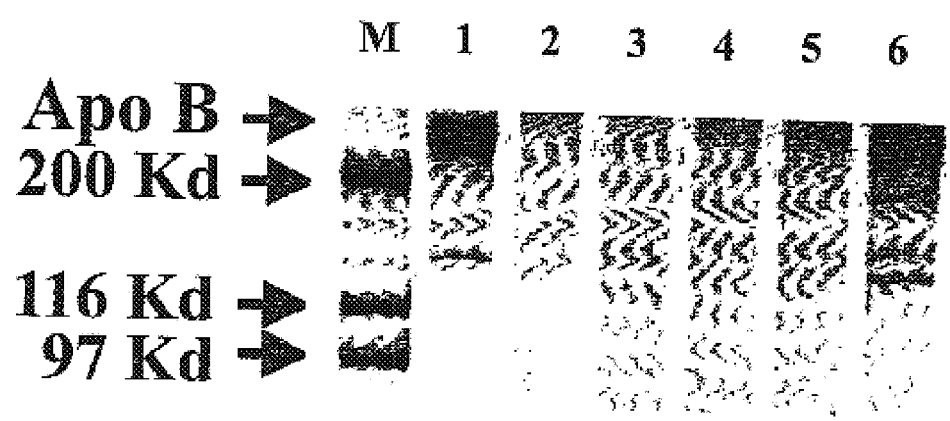
FIG. 5 is a graph showing Inhibition of $Cu^{2+}$ mediated Apo B fragmentation in LDL by various concentrations of HSE.

$CU^{2+}$ may induce the oxidation of LDL and then cause Apo B fragmentation in LDL. LDL (120 g/ml) was incubated with 10 $\mu$M $CuSO_4$ at 37° C. in the presence of HSE for 4 hours. After the incubation, EDTA (final concentration 1 mM) was added to prevent any further oxidation. Approximately 6 mg protein of the LDL was applied to SDS-PAGE (315% gradient). After the electrophoresis, each spot was stained with Coomassie Brilliant blue R250. M, standard molecular weight markers. It is observed that the higher the concentration of HSE is, the less the Apo B fragmentation in LDL is caused, i.e., the higher the concentration of HSE is, the more significantly the oxidation of LDL is countered. The results are shown in FIG. 5.

EXAMPLE 2

Decreasing Triglyceride or Cholesterol Levels in Plasma

30 New Zealand rabbits (2000–2200 g) and 24 Sprague-Dawley rats(200–220 g) were used for the following experiments. The rabbits were split into five groups, each rabbit was cooped in a cage and fed with 150 g diet every day for 10 weeks. The diet of 3 groups contained 1.3% cholesterol and 3% lard oil (i.e. cholesterol-fed diet) in order to induce atherosclerosis. The diet of the other 2 groups contained 1% and 0.5% HSE respectively.

The rats were split into four groups, 6 rats were cooped in a cage and each rat was fed with 25 g diet every day for 12 weeks. The diet of 2 groups contained 1.3% cholesterol and 3% lard oil in order to induce atherosclerosis. The diet of the other 2 groups contained 1% and 2% HSE respectively.

Figure 6:
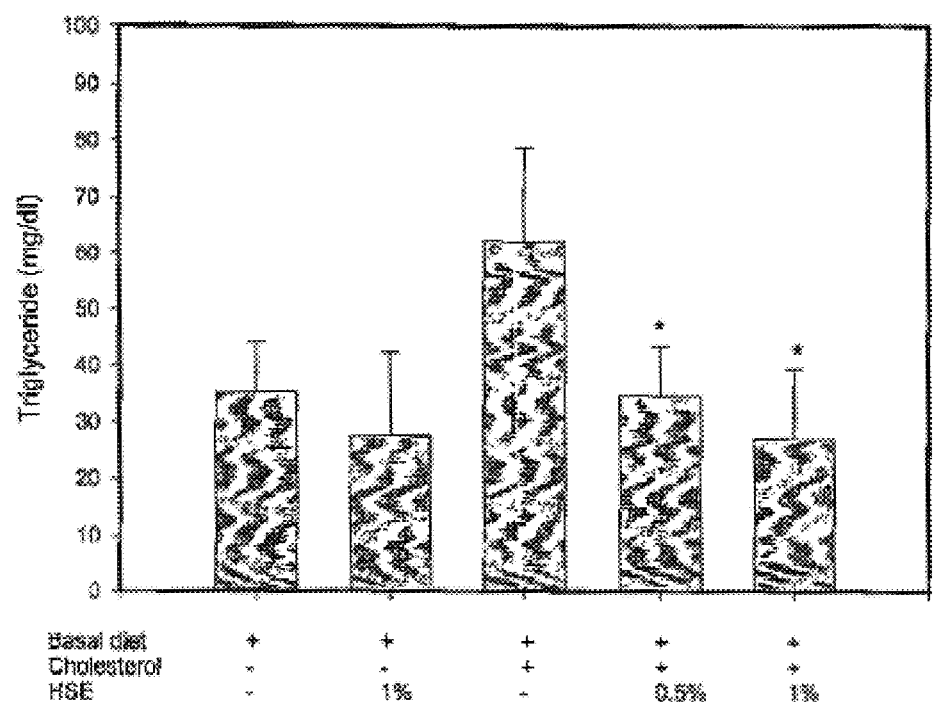
FIG. 6 is a chart comparing the effect of various concentrations of HSE on plasma triglyceride levels in 10 week-period cholesterol fed rabbits. The cholesterol fed diet containing 1.3% cholesterol and 3% lard oil. * $p<0.05$, compared with the group of cholesterol fed.
Figure 7:
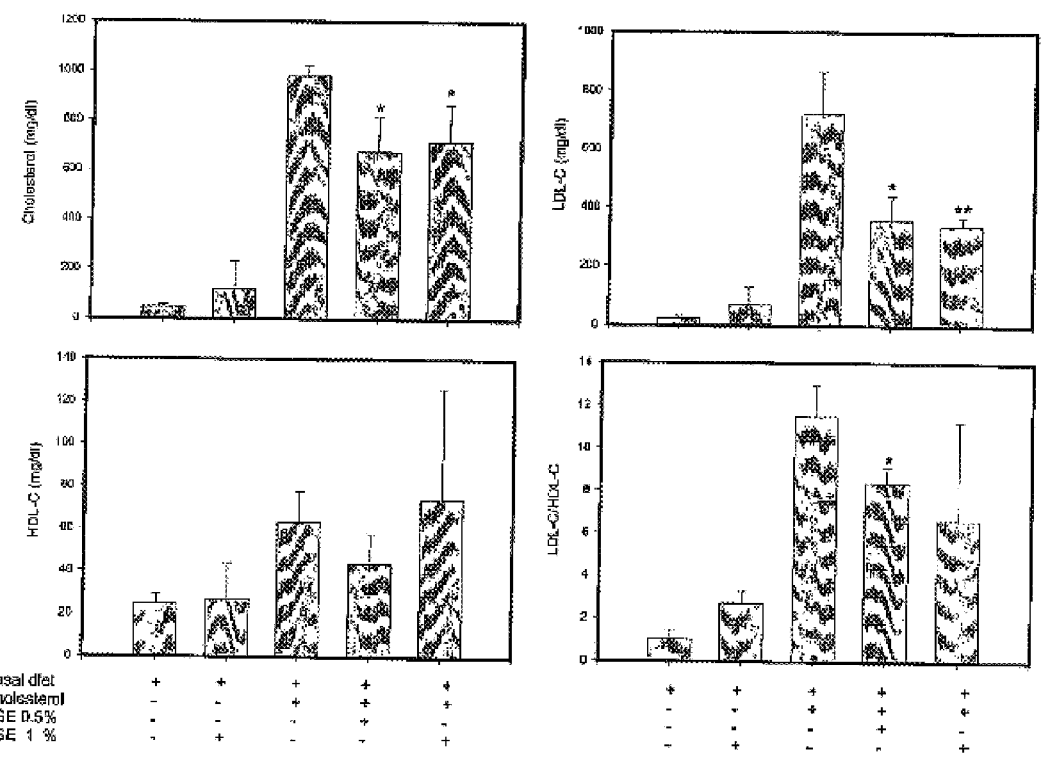
FIG. 7 is a chart comparing the effect of various concentrations of HSE on plasma cholesterol levels in 10 week-period cholesterol fed rabbits. The cholesterol fed diet containing 1.3% cholesterol and 3% lard oil. * $p<0.05$; ** $p<0.01$, compared with the group of cholesterol fed.

After having been fed for ten weeks, the rabbits were anesthetized using sodium pentothal (16 mg/kg, i.v.) and then sacrificed. The blood was collected in the EDTA-coated tubes, and then centrifugated for the purpose of analyzing plasma lipid levels including plasma triglyceride levels and plasma cholesterol levels. The study shows adding HSE in the cholesterol-fed diet is capable of decreasing plasma triglyceride levels (p<0.05). The results are shown in FIG. 6. Cholesterol-fed diet fed rabbits raised their plasma cholesterol levels up to 8.4 folds, their LDL-C levels up to 10.5 folds, LDL-C/HDL-C ratios up to 4.4 folds from the original levels; adding 0.5% HSE in the cholesterol-fed diet is capable of decreasing plasma cholesterol levels, LDL-C levels and LDL-C/HDL-C ratios (p<0.05), adding 1% HSE in the cholesterol-fed diet is capable of decreasing plasma cholesterol levels, LDL-C levels and LDL-C/HDL-C ratios (p<0.01). The results are shown in FIG. 7.

Figure 8:
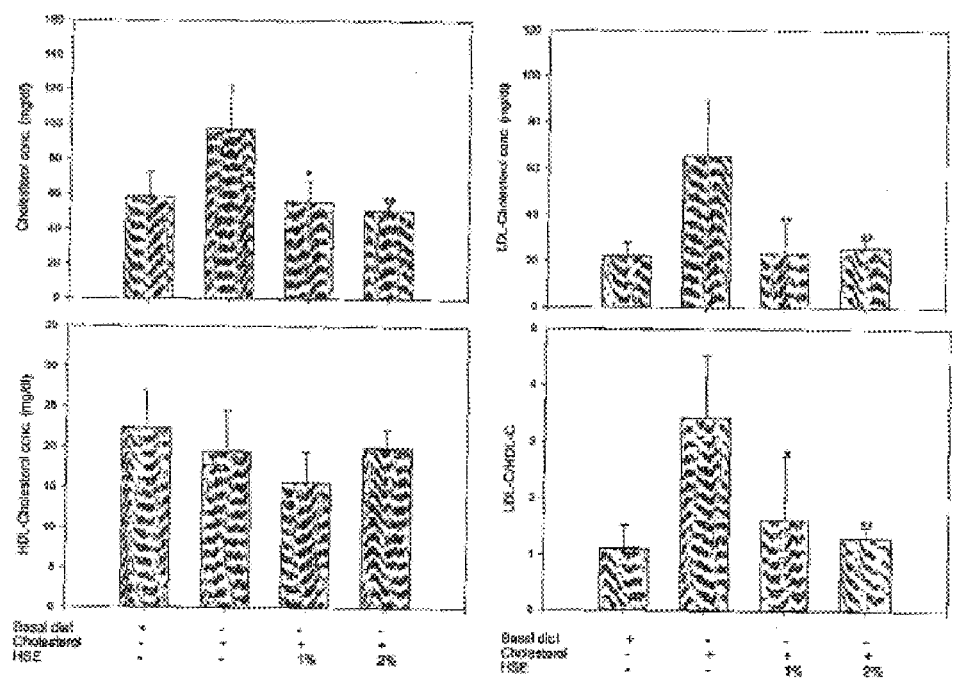
FIG. 8 is a chart comparing the effect of various concentrations of HSE on plasma lipid levels in 12 week-period cholesterol fed rats. The cholesterol fed diet containing 1.3% cholesterol and 3% lard oil. * $p<0.05$; ** $p<0.01$, compared with the group of cholesterol fed.

The rats were sacrificed after having been fed for twelve weeks. The blood was collected in the EDTA-coated tubes, and then centrifugated for the purpose of analyzing plasma cholesterol levels. It is observed that Cholesterol-fed diet fed rats raised their plasma cholesterol levels up to 1.6 folds, their LDL-C levels up to 3 folds, LDL-C/HDL-C ratios up to 2.6 folds from the original levels; adding 1% HSE in the cholesterol-fed diet is capable of decreasing plasma cholesterol levels, LDL-C levels and LDL-C/HDL-C ratios (p<0.05), adding 2% HSE in the cholesterol-fed diet is capable of decreasing plasma cholesterol levels, LDL-C levels and LDL-C/HDL-C ratios (p<0.01). The results are shown in FIG. 8. Thus, it is further proven that the HSE can decrease triglyceride or cholesterol levels in plasma.

EXAMPLE 3

Inhibition of Atherosclerosis

Figure 9:
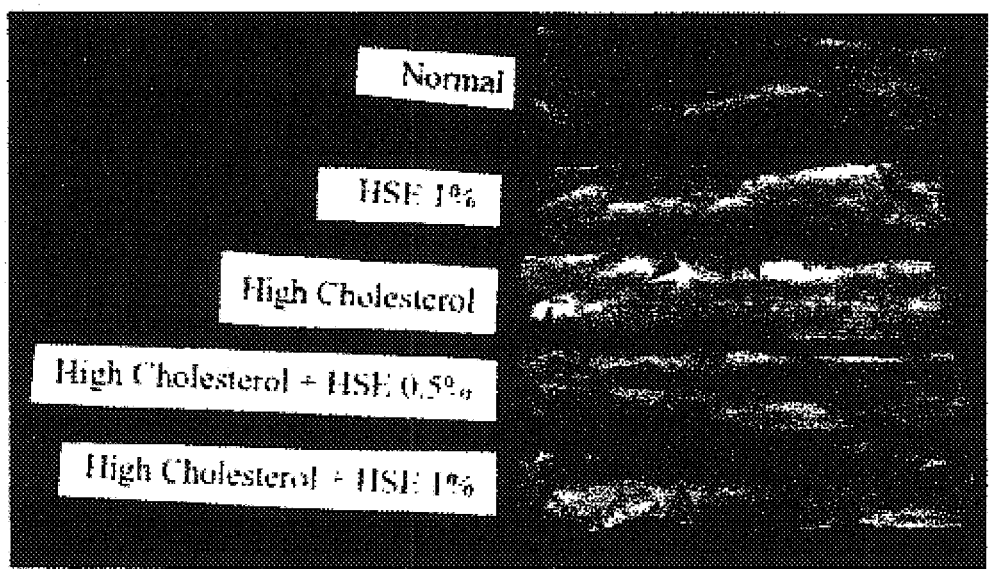
FIG. 9 is a graph showing Internal surface of the thoracic aortas from the five groups of rabbits showing Oil red O stainable lipid deposit.

Lipid deposit in the endothelium cells of arteriae often leads to atherosclerosis, that is, if the lipid deposit in the endothelium cells of arteriae has reached certain amount, then it is quite possible that atherosclerosis may occur. In this study, we stained the chest arteriae of the rabbits recited in example 2 to discover the conditions of lipid deposit. This study shows there is much deposit in the arteriae' endothelium cells of those rabbits fed with Cholesterol-fed diet, however, the lipid deposit substantially decreased accompanying the addition of HSE. The results are shown in FIG. 9.

Figure 10:
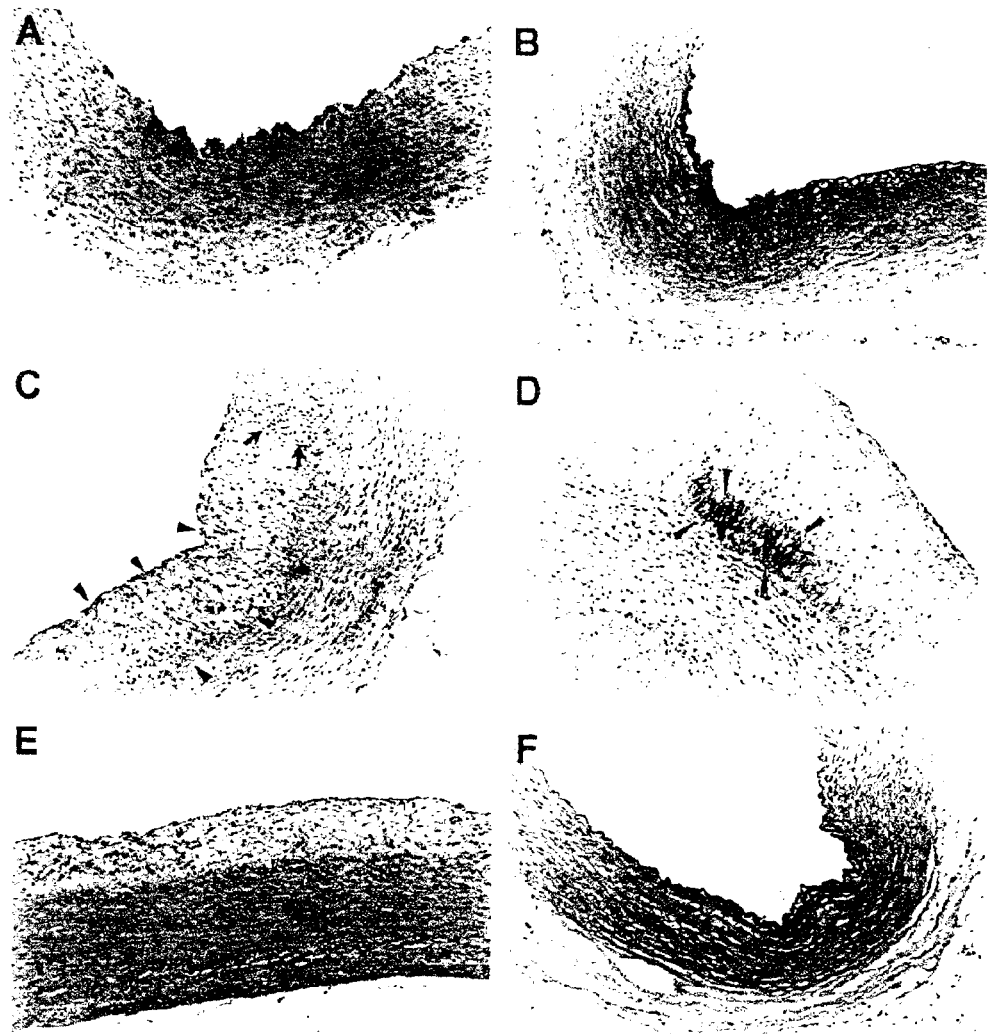
FIG. 10 is a graph showing Histological analysis of a representative atherosclerotic lesion from cholesterol-fed rabbits treated for 10 weeks with HSE 0.5% and HSE 1%. Basal diet (A); rabbits fed basal diet with HSE 1% (wt/wt) (B); rabbits fed with high cholesterol diet containing 3% lard oil and 1.3% cholesterol on basal diet (C and D). The arrow was shown for foam cell ( ) and smooth muscle cell migration ( ) in (C); The calcification core was shown as arrow ( ) in (D); high cholesterol diet fed rabbits and treated with HSE 0.5% (E) and 1% (F) on daily diet.

Furthermore, we pathologically biospied the arteriae of the rabbits recited in example 2 and found that no foam cells formed in the arteriae of the rabbits fed with Cholesterol-fed diet added with 0.5% HSE or 1% HSE and fed with Basil diet. In addition, no migration of smooth muscle cells or formation of calcification core was found. The results are shown in FIG. 10.

EXAMPLE 4

No Side-Effect on Hepatic Function and Renal Function

The rabbits were fed with Basil diet and Basil diet added with 1% HSE respectively, The rats were fed with Basil diet and Basil diet added with 2% HSE respectively. It is observed that there is no substantial difference between the measurements of ALT, AST, ALP of both groups. Thus, it is proven that HSE does not make harm to hepatic function. The results are shown in FIG. 11.

The rabbits were fed with Basil diet and Basil diet added with 1% HSE respectively, The rats were fed with Basil diet and Basil diet added with 2% HSE respectively. It is observed that there is no substantial difference between the measurements of BUN, AST, ALP of both groups. Thus, it is proven that HSE does not make harm to renal function. The results are shown in FIG. 12.

What is claimed is:

1. A method of treating a patient suffering from artheroselerosis said method, comprises administering an effective amount of a *Hibiscus sabdariffa* water extract to said patient suffers from artherosclerosis wherein oxidation of low density lipoproteins is decreased by the administration of *Hibiscus sabdariffa* water extract.

2. The method of claim 1, further comprising said *Hibiscus sabdariffa* water extract with a pharmaceutically acceptable carrier.

3. The method of claim 2, wherein the *Hibiscus sabdariffa* water extract is administered orally.

4. The method of claim 3, wherein the administration is in tablet or capsule form.

* * * * *